United States Patent [19]

Chambron

[11] Patent Number: 4,545,571
[45] Date of Patent: Oct. 8, 1985

[54] LINEARLY DISPLACEABLE EXAMINATION TABLE

[75] Inventor: Edmond Chambron, Paris, France

[73] Assignee: Thomson-CSF, Paris, France

[21] Appl. No.: 502,165

[22] Filed: Jun. 8, 1983

[30] Foreign Application Priority Data

Jun. 11, 1982 [FR] France ............................ 82 10241

[51] Int. Cl.[4] ............................................. G01N 23/04
[52] U.S. Cl. .................................... 269/322; 378/209
[58] Field of Search ............... 14/69.5, 71.1; 378/208, 378/209, 177; 108/137, 143; 384/418, 419; 269/322, 323, 71

[56] References Cited

U.S. PATENT DOCUMENTS

| | | | |
|---|---|---|---|
| 3,588,500 | 6/1971 | Koerner | 269/323 |
| 3,715,769 | 2/1973 | Mori et al. | 14/71.1 |
| 4,452,558 | 6/1984 | Muraguchi | 269/289 MR |

FOREIGN PATENT DOCUMENTS

| | | | |
|---|---|---|---|
| 2008251 | 10/1970 | Fed. Rep. of Germany . | |
| 1551249 | 12/1968 | France . | |
| 173142 | 12/1921 | United Kingdom | 384/418 |

Primary Examiner—Robert C. Watson

[57] ABSTRACT

A patient-bearing panel is displaceable in a longitudinal direction (y—y) under conditions which enable the panel to be made entirely of material which is a poor absorber of X-rays and which is also uniform in its absorption. The panel has an end overhanging a first roller by an amount which varies as a function of its longitudinal displacement.

10 Claims, 4 Drawing Figures

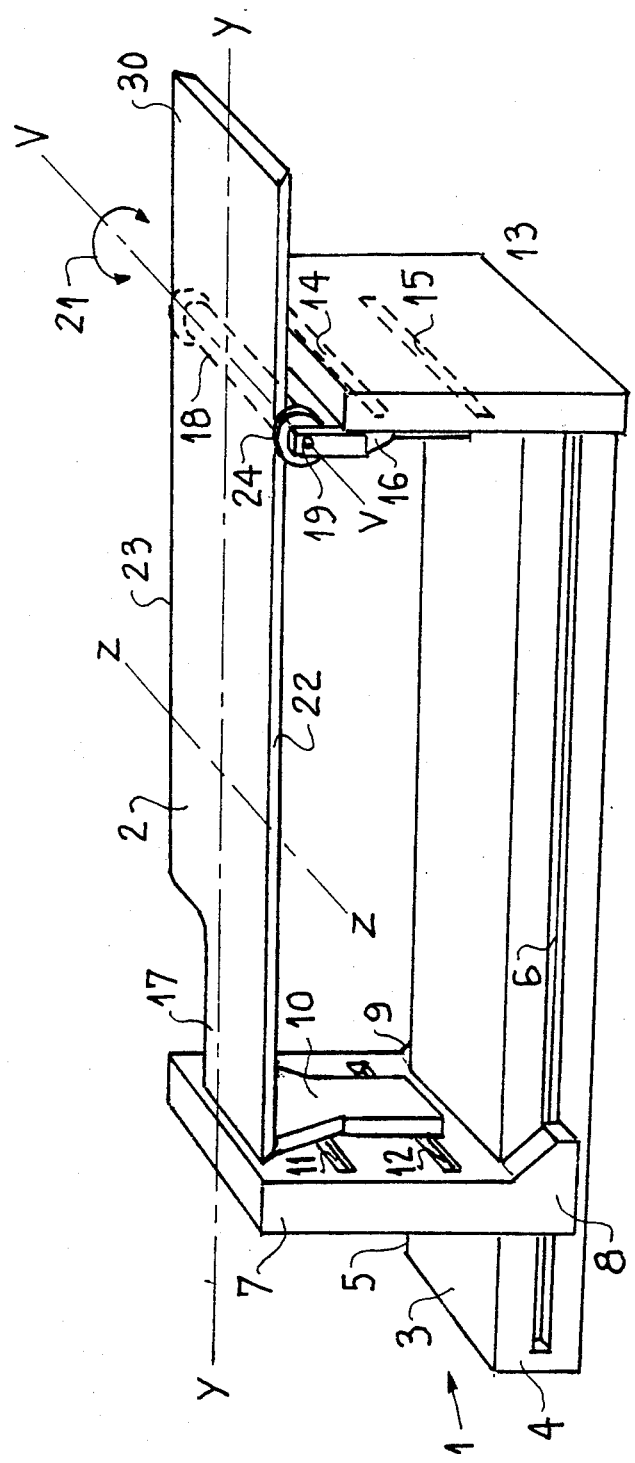
FIG_1

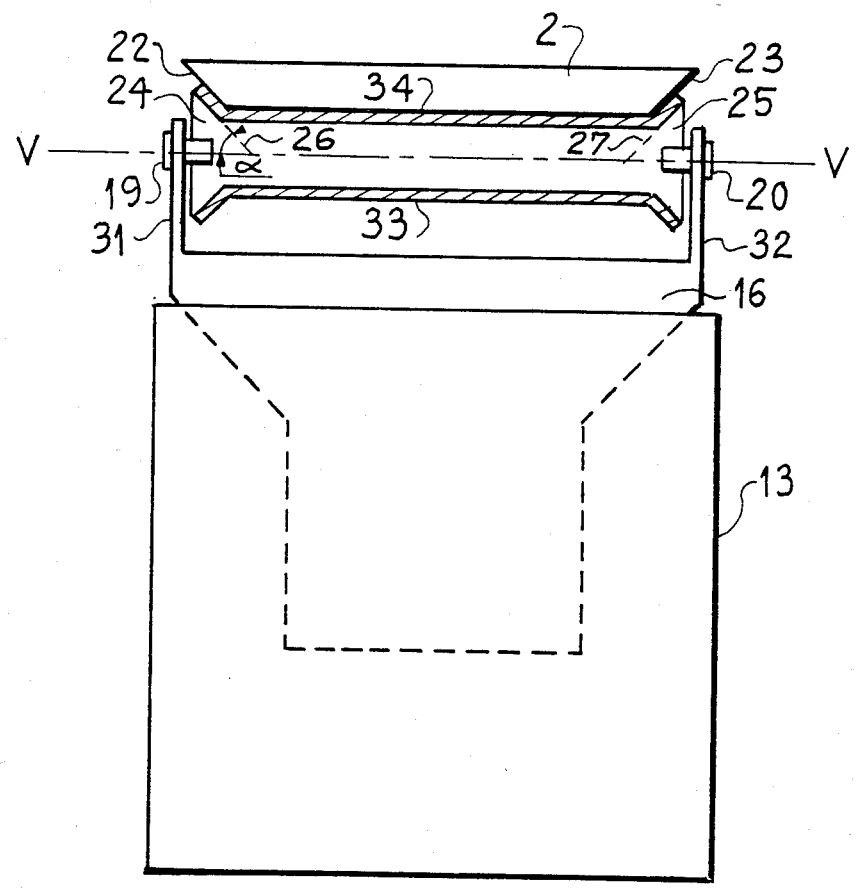

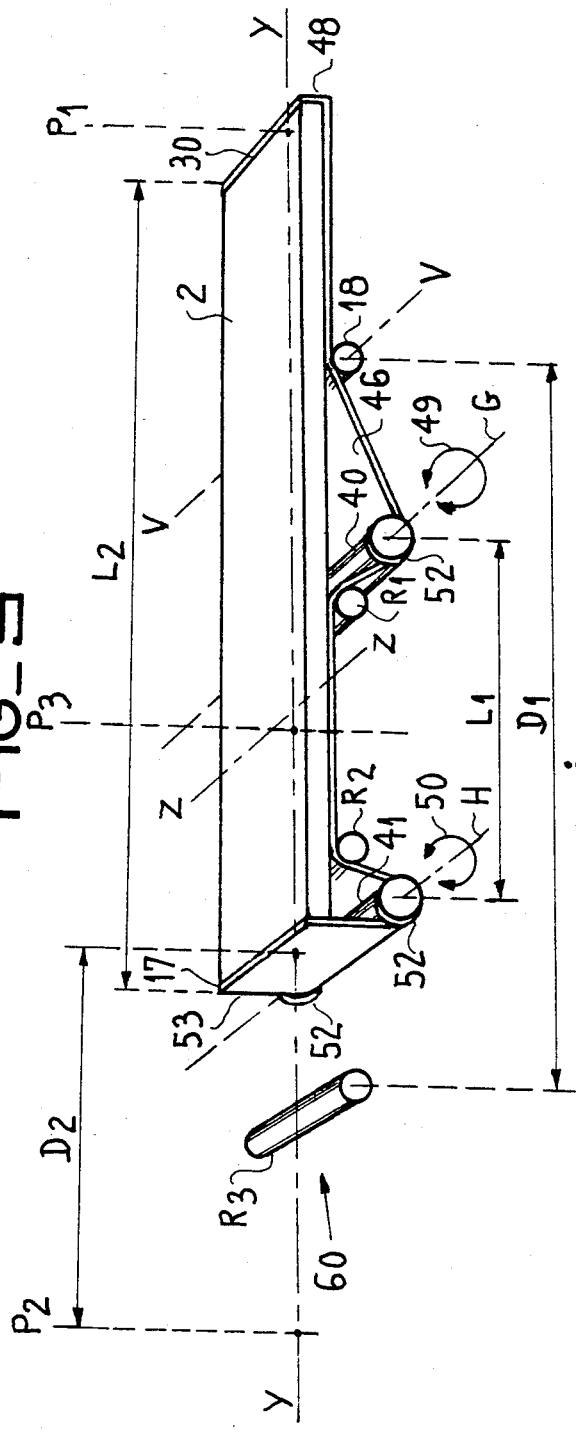
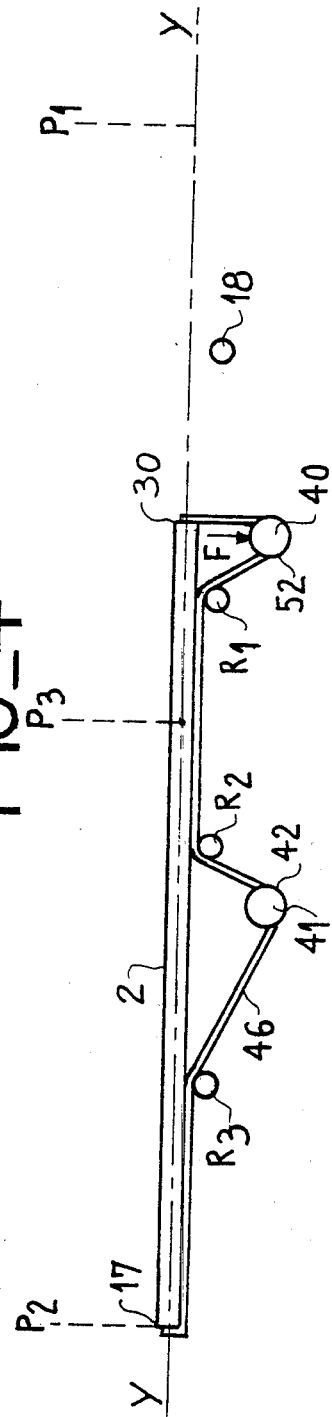

LINEARLY DISPLACEABLE EXAMINATION TABLE

The present invention relates to an examination table having a patient-bearing panel which is displaceable along a longitudinal axis, eg. for use in radiology.

BACKGROUND OF THE INVENTION

When patients are examined by means of rays, usually X-rays, there is a need to be able to direct the rays through any selected part of the patient from the head to the feet and at various angles such as frontally or sideways. A longitudinally displaceable patient-bearing panel can facilitate such examination.

With existing equipment, there is a problem with sideways investigations, in that the radiation applied to the patient is absorbed in a discontinuous manner by the patient-supporting panel because the long sides thereof are provided with panel-guiding means for enabling said longitudinal displacement. The panel guiding means are generally made of metal, and absorb patient-investigating rays far more than does the rest of the material from which the panel is made.

One proposed solution has been to provide such guiding means along only one half of the panel length. While mitigating the above problem, such a solution is still not very satisfactory when investigating a patient from heat to foot.

Preferred embodiments of the present invention provide an examination table having a longitudinally displaceable patient-bearing panel which absorbs patient-investigating rays little and uniformly over its entire length. In particular, an examination table in accordance with the invention has no need for extra parts along the sides of the panel.

SUMMARY OF THE INVENTION

The present invention provides an examination table having an elongate patient-bearing panel which is longitudinally displaceable parallel to the longitudinal first axis, wherein the table comprises: said patient-bearing panel; a first roller disposed to rotate about a roller axis which is transverse to said longitudinal first axis and fixed relative thereto, said patient-bearing panel resting on said roller and having an end overhanging beyond said roller by an amount which varies as a function of the longitudinal displacement of the panel; and means for supporting the other end of the panel.

BRIEF DESCRIPTION OF THE DRAWINGS

Two embodiments of the invention are described by way of example with reference to the accompanying drawings, in which:

FIG. 1 is a diagrammatic perspective view of a first examination table in accordance with the invention;

FIG. 2 is a diagrammatic end view of the table shown in FIG. 1;

FIG. 3 is a diagrammatic perspective side view of a patient-bearing panel and its associated support means in a second embodiment of the invention; and FIG. 4 is a diagrammatic elevation of the items shown in FIG. 3.

MORE DETAILED DESCRIPTION

FIG. 1 shows an examination table 1 including, in particular, a patient-bearing panel 2 which is movable along a first longitudinal axis y—y. The table 1 may include means suitable for examining a patient, but such means are not shown, in order to clarify the description.

A base 3 serves to support the table 1 and has two longitudinal sides 4 and 5 each of which includes a first longitudinal groove 6, only one of which is visible in the drawing, namely that extending along the side 4. The first grooves 6 constitute a first displacement path which is parallel to the axis y—y and which guides a moving first riser 7 which has feet 8 and 9 fitted with running gear (not shown) and engaged in the first grooves 6.

The moving first riser 7 is associated with a moving second riser 10 which likewise includes running gear (not shown) enabling the second riser 10 to co-operate with second grooves 11 and 12 constituting a second displacement path for the second riser 10. Said second path extends parallel to a second axis z—z which itself extends transversely across the longitudinal axis y—y.

The table 1 also includes a fixed third riser 13 which has third grooves 14 and 15 (shown in dashed lines in FIG. 1) providing a third displacement path for a moving fourth riser 16. Like the other moving risers, the moving fourth riser includes running gear (not shown) engaged in the third grooves 14 and 15 in such a manner as to enable the moving fourth riser 16 to move parallel to the transverse axis z—z.

One end 17 of the panel 2 is fixed to the moving second riser 10 which, together with the moving first riser 7, constitutes a first support means for said panel 2.

The panel 2 also rests on a second support means which is constituted in the non-limiting example here described by a first roller 18 drawn in dashed lines in FIG. 1. The roller 18 is disposed across the panel 2 along a third axis v—v which is parallel to the axis z—z. The ends of the roller 18 are fixed to the moving fourth riser 16 by fixing means 19 and 20 in such a manner as to be capable of rotating about said third axis v—v in the directions of an arrow 21. Only the fixing means 19 are visible in FIG. 1.

This arrangement enables the panel 2 to move longitudinally, either by motor or by hand, the panel 2 being supported by the first roller 18 and by the first support means constituted by the moving first and second risers 7 and 10 guided by the first grooves 6 for longitudinal displacement. In such displacement, the first roller 18 is caused to rotate, but remains fixed relative to the first axis y—y. Depending on its displacement, a variable length of the end 30 of the panel 2 overhangs beyond the third and fourth risers 13 and 16. Lateral support is provided at the roller 18 by side stops 24 and 25 which co-operate with the long edges or sides 22 and 23 of the panel 2. The side stop 25 is hidden in FIG. 1, but can be seen in FIG. 2.

The panel 2 may also be moved in parallel with the transverse second axis z—z by means for moving the second and fourth risers 10 and 16 co-operating during transverse movement with the second and third grooves 11, 12 and 14, 15 respectively.

This is an important feature of an examination table 1 in accordance with the invention, i.e. a patient-bearing panel 2 is moved and guided linearly without any need to fix moving or guiding means to the sides of the panel. Over the entire length of a patient (not shown) the panel 2 is made solely of a material which is a poor and uniform absorber of the rays used for examining the patient.

FIG. 2 shows a portion of the table 1 in accordance with the invention seen end on from the end having the first roller 18. The figure is schematic, showing only the panel 2 and the above-mentioned means necessary for guiding it.

In the non-limiting example described, the side stops 24 and 25 are integral portions of the the roller 18, being constituted by the ends thereof and rotating therewith about the third axis v—v.

The side stops 24 and 25 are conical in shape having generator lines 26 and 27 which lie parallel to the longitudinal sides 22 and 23 of the panel 2, and which are at 45° to the third axis v—v in the example here described.

The moving fourth riser 16, as supported by the fixed third riser 13, includes two arms 31 and 32 between which the first roller 18 is suspended. The roller 18 is fixed thereto by the fixing means 19 and 20 which leave it free to rotate about the third axis v—v. This rotation is obtained during longitudinal displacement of the panel 2 by virtue of the panel resting on the roller 18. The outside surface of the roller 18 is covered with a flexible material 33 which, in the present non-limiting example, is constituted by rubber. The flexible material 33 serves to even out the contact pressure forces between the first roller 18 and the bottom face 34 of the panel 2.

The above description demonstrates that a patient-bearing panel 2 is displaceable along a longitudinal first axis y—y or along a second axis z—z transverse to the first axis. By virtue of its co-operation with the means such as the first roller 18 and its side stops 24 and 25, the panel 2 does not need additional guide pieces to be applied to its long sides. In addition to the radiation-absorbing advantage obtained thereby, this makes it possible for the panel 2 to be much lighter and easier to handle than patient-bearing panels in prior art examination rooms.

FIG. 3 shows another version of the invention, in which the panel 2 is supported by the first roller 18 co-operating with a first support means 60 constituted by a plurality of second rollers R1, R2 and R3.

During longitudinal displacement, the panel 2 is kept parallel to the longitudinal first axis y—y, by two guide rollers 40 and 41 which co-operate with a flexible strip 46.

The first roller 18 and the second rollers R1, R2 and R3 are supported by risers of the table 1 which are not shown (nor is the rest of the table 1) in the interests of clarity in the description.

The first roller 18 is disposed transversely to the panel 2, having an axis of rotation v—v which is parallel to the second axis z—z as in the first embodiment described above. The second rollers R1, R2 and R3 are three in number and are disposed about respective axes (not shown) which lie parallel to the said second axis z—z. Each of the second rollers is rotatable about its axis when the panel 2 is moved longitudinally in the same manner as the first roller 18.

The first roller 18 and the second rollers R1, R2 and R3 are spaced out along the longitudinal first axis y—y over a length L1 which is less than the length L2 of the panel 2. The rollers are so disposed that the panel 2 is always supported on at least three of them throughout its longitudinal displacement between extreme positions P1 and P2, ie. the rollers are disposed so that the distance D1 between the first roller 18 and the second roller R3 which is furthest away therefrom is not greater than the length L2 of the panel 2.

The flexible strip 46 is made of a material which is a poor absorber of X-rays, eg. Mylar a few tenths of a mm thick, and it is fixed at its ends 47 and 48 to respective ends 17 and 30 of the panel 2. The strip 46 moves at the same time as the panel 2 and is held taut against the bottom face 34 of the panel 2 before being deflected away therefrom to pass around the guide rollers 40 and 41 (the number of guide rollers being two in this non-limiting example).

The guide rollers 40 and 41 rotate in either direction, as shown by arrows 49 and 50, about respective axes G and H which are parallel to the transverse second axis z—z. The guide rollers are located below the level of the first roller 18 and the second rollers R1, R2 and R3, and the ends of the guide rollers are provided with second side stops 52 serving to guide and to hold the sides 53 and 54 of the strip 46, and to prevent them from moving sideways.

This is an important feature of the invention since it ensures that the panel 2 is held parallel to the longitudinal first axis y—y during longitudinal displacement. This is achieved by virtue of the second side stops 52 co-operating with the flexible strip 46 whose ends are fixed to the ends 17 and 30 of the panel 2.

In the example shown in FIG. 3, the panel 2 is at one end of its travel with its end 30 co-inciding with the extreme position P1. In this position it can be seen:

firstly that the panel 2 is supported by the first roller 18 and by two of the second rollers R1 and R2; and secondly that starting from the second end 30 of the panel 2, the strip 46 is initially held taut against the panel under face 34 until it passes over the first roller 18 where it leaves the under face 34 to pass round one of the guide rollers 40. It then passes back over the second roller R1 and is again held taut against the under face 34 for a second run until it reaches the next one of the second rollers R2 after which it again leaves the under face 34 to pass round the other guide roller 41 before returning to panel 2, this time at its first end 17.

In the non-limiting example described, the two guide rollers 40 and 41 are separated by a distance L1, where L1 is less than the travel D2 of the panel 2, ie. the distance between the end 17 of the panel 2 and the extreme position P2 when the panel is in the opposite extreme position as shown in FIG. 3. The guide rollers 40 and 41 are symmetrically disposed on either side of a mid position P3 half way between the extreme positions P1 and P2, and the distance L1 between the guide rollers 40 and 41 and the length L2 of the panel 2 are such that when one or other of the panel ends 17 and 30 is in the corresponding extreme position P2 of P1 respectively, then the other end 30 or 17 extends at least as far as the further one of the guide rollers.

FIG. 4 is a diagram showing the panel 2 in its other longitudinally extreme position, ie. as far as possible to the left (as seen in the figures) of the mid position P3. The end 17 is thus in the extreme position P2, while the end 30 is directly above the guide roller 40. The panel 2 is then supported by three second rollers R1, R2 and R3 leaving the first roller 18 empty. The strip 46 is in a position which is symmetrical relative to the position shown in FIG. 3.

This arrangement prevents the panel 2 from tipping up when either of its ends 30 or 17 is overhanging in the corresponding extreme position P1 or P2. Tipping is avoided by the opposite end of the panel 2 then being held down by the strip 46 where it passes round the corresponding guide roller 40 or 41.

Means may be provided for putting the strip 46 under tension: for example, one of the guide rollers, say the guide roller 40, could co-operate in conventional manner with means (not shown) for exerting a force F in a suitable direction away from the panel 2.

The above description shows how a panel 2 may be displaced along a longitudinal axis y—y supported solely by three or four of the rollers 18, R1, R2 and R3, and held sideways by virtue of the side stops 52 on the guide rollers co-operating with the flexible strip 46.

It should be observed that, as in the first embodiment described above, the long sides of the panel 2 have no need for additional guide means.

I claim:

1. An x-ray examination table comprising: an elongate patient-bearing panel of a material which is a poor and uniform absorber of x-rays, said panel being longitudinally displaceable parallel to the longitudinal first axis, a first roller disposed to rotate about a roller axis which is transverse to said longitudinal first axis and fixed relative thereto, means for supporting said first roller, said patient-bearing panel resting on said roller and having an end overhanging beyond said roller by an amount which varies as a function of the longitudinal displacement of the panel; and means for supporting the other end of the panel so as to be displaceable parallel to said longitudinal first axis, said means for supporting said roller and said means for supporting the other end of the panel being displaceable parallel to a second axis which extends transverse to said longitudinal first axis.

2. An examination table according to claim 1, further including first side stops co-operating with the long sides of the panel to provide lateral guidance to said panel during its longitudinal displacement.

3. An examination table according to claim 2, wherein said first side stops are fixed to said first roller and are rotatable therewith about the roller axis.

4. An examination table according to claim 2, wherein said first side stops and said roller are covered by a flexible material for evening out contact forces with the panel.

5. An examination table according to claim 2, wherein said first side stops are conical in shape, each having a generator line which is parallel to the corresponding long side of the panel.

6. An examination table according to claim 5, wherein the generator lines of the connical side stops are all at angles of 45° to the roller axis of said first roller.

7. An examination table according to claim 1, wherein said means for supporting the other end of the panel is constituted by a plurality of second rolles rotatably about respective axes parallel to the axis of the first roller and spaced out along said longitudinal first axis to support said panel during longitudinal displacement between two extreme position in which one or the other end of the panel overhangs beyond the corresponding end one of the rollers, the panel being backed by a strip of flexible material which co-operates with guide rollers in such a manner that when one end of the panel is overhanging beyond a roller, the opposite end of the panel is held by said strip and at least one of said guide rollers to prevent the panel from tipping.

8. An examination table according to claim 7, wherein the said flexible strip has ends fixed to respective ends of the panel, and wherein said flexible strip co-operates with said guide rollers to keep the panel parallel to said longitudinal first axis during longitudinal displacement.

9. An examination table according to claim 7, wherein the guide rollers include second side stops co-operating with the edges of the flexible strip to keep the panel parallel to said longitudinal first axis during longitudinal displacement.

10. An examination table according to claim 7 wherein the flexible strip is made of Mylar.

* * * * *